(12) United States Patent
Gutowska et al.

(10) Patent No.: US 6,660,247 B1
(45) Date of Patent: Dec. 9, 2003

(54) MULTIPLE STIMULUS REVERSIBLE HYDROGELS

(75) Inventors: Anna Gutowska, Richland, WA (US); Karol J. Krzyminski, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 09/603,730

(22) Filed: Jun. 23, 2000

(51) Int. Cl.[7] .............................................. A61K 49/00
(52) U.S. Cl. ...................... 424/9.1; 424/1.11; 424/400; 424/422
(58) Field of Search .............................. 424/1.11–1.65, 424/9.1, 422, 400, 423, 426

(56) References Cited

U.S. PATENT DOCUMENTS

| | | | |
|---|---|---|---|
| 4,732,930 A | 3/1988 | Tanaka et al. | 524/742 |
| 5,213,580 A | 5/1993 | Slepian et al. | |
| 5,252,318 A * | 10/1993 | Joshi et al. | 424/78.04 |
| 5,256,765 A | 10/1993 | Leong | |
| 5,410,016 A | 4/1995 | Hubbell et al. | |
| 5,514,379 A | 5/1996 | Weissleder et al. | |
| 5,525,334 A | 6/1996 | Ito et al. | 424/78.35 |
| 5,575,815 A | 11/1996 | Slepian et al. | |
| 5,589,568 A | 12/1996 | Higashijima et al. | 530/324 |
| 5,634,946 A | 6/1997 | Slepian | |
| 5,662,609 A | 9/1997 | Slepian | |
| 5,674,287 A | 10/1997 | Slepian et al. | |
| 5,695,480 A | 12/1997 | Evans et al. | 604/264 |
| 5,702,361 A | 12/1997 | Evans et al. | 604/53 |
| 5,749,922 A | 5/1998 | Slepian et al. | |
| 5,766,704 A | 6/1998 | Allen et al. | 428/34.1 |
| 5,843,156 A | 12/1998 | Slepian et al. | |
| 5,858,746 A | 1/1999 | Hubbell et al. | 435/177 |
| 5,876,741 A * | 3/1999 | Ron | 424/423 |
| 5,939,485 A | 8/1999 | Bromberg et al. | 524/556 |
| 5,942,209 A | 8/1999 | Leavitt et al. | |
| 5,976,648 A | 11/1999 | Li et al. | 428/34.9 |
| 6,090,911 A * | 7/2000 | Petka et al. | 530/300 |
| 6,113,629 A | 9/2000 | Ken | 623/1.1 |
| 6,352,682 B2 | 3/2002 | Leavitt et al. | |
| 2002/0168319 A1 | 11/2002 | Filler et al. | |

FOREIGN PATENT DOCUMENTS

| | | |
|---|---|---|
| EP | 0 704217 | 4/1996 |
| JP | 09154573 | 6/1997 |
| WO | WO 96/03112 | 2/1996 |
| WO | WO 97/33628 | 9/1997 |
| WO | WO 98/55147 | 12/1998 |
| WO | WO99.55386 * | 11/1999 |
| WO | WO 99/56783 | 11/1999 ..................... 47/30 |
| WO | WO 00/43355 | 7/2000 ................. 233/38 |
| WO | WO 00/45868 | 8/2000 ....................... 24/6 |

OTHER PUBLICATIONS

Gutowska et al., "Thermosensitive Polymers for Drug Delivery," *American Chemical Society*, vol. 37, No. 2, pp. 115–116 (1996).

Ganorkar et al., "Loading and Release Studies Using pH/Temperature–Sensitive Polymers for Oral Protein Delivery," *Proceed. Int'l. Symp. Control. Rel. Bioact. Mater.*, pp. 501–502 (1998).

Hattori et al., "Copolymers containing isopropyl acrylamide for temperature–regulated absorption of nucleic acids during preparation of enzyme," (Abstract).

Teramoto et al., "Phase transition for aqueous solution of polyelectrolyte complex containing N–isopropylamide," (Abstract).

G Chen et al., "*Graft Copolymers That Exhibit Temperature–Induced Phase Transitions Over a Wide Range of pH*", p. 49–52, 1995.

TG Park, "*Temperature Modulated Protein Release from pH/Temperature–Sensitive Hydrogels*", p. 517–521. 1999.

J Zhang et al., "*Synthesis and Characterization of pH– and Temperature–Sensitive Poly(methacrylic acid)/Poly(N–isopropylacrylamide) Interpenetrating Polymeric Networks*", p. A–F. 1999.

S Beltran et al., "*Swelling Equilibria for Weakly Ionizable, Temperature–Sensitive Hydrogels*", p. 1–2. 1991.

TG Park et al., "*Synthesis, Characterization, and Application of pH/Temperature Sensitive Hydrogels*", p. 112–113, 96. 1990.

* cited by examiner

*Primary Examiner*—Dameron L. Jones
(74) *Attorney, Agent, or Firm*—Klarquist Sparkman, LLP

(57) ABSTRACT

A polymeric solution capable of gelling upon exposure to a critical minimum value of a plurality of environmental stimuli is disclosed. The polymeric solution may be an aqueous solution utilized in vivo and capable of having the gelation reversed if at least one of the stimuli fall below, or outside the range of, the critical minimum value. The aqueous polymeric solution can be used either in industrial or pharmaceutical environments. In the medical environment, the aqueous polymeric solution is provided with either a chemical or radioisotopic therapeutic agent for delivery to a specific body part. The primary advantage of the process is that exposure to one environmental stimuli alone will not cause gelation, thereby enabling the therapeutic agent to be conducted through the body for relatively long distances without gelation occurring.

31 Claims, 3 Drawing Sheets

P(NIPA-co-DMAEA) = 97-3 mol %, 10 wt % solutions

P(NIPA-co-AAc) = 97.8-2.2 mol %, 10 wt % solutions

US 6,660,247 B1

MULTIPLE STIMULUS REVERSIBLE HYDROGELS

This invention was made with Government support under Contract No. DE-AC06-76RL01830 awarded by the U.S. Department of Energy. The U.S. Government has certain rights in the invention.

FIELD OF THE INVENTION

The present invention relates in general to reversible gel compounds in which gelation is the result of response to a plurality of environmental stimuli. More particularly, the present invention is directed to polymeric solutions which gel in response to exposure to a critical minimum value of at least two environmental stimuli, such as in vivo stimuli found in human or other mammalian bodies. The gelation response can be reversed by reducing the value of at least one of such environmental stimuli to less than (or outside the range of) the critical minimum value.

BACKGROUND OF THE INVENTION

The use of reversible gelling compounds is well known in the art. In the context of this art, "gel" means a form of material between the liquid and solid state that consists of physically crosslinked networks of long polymer molecules with liquid molecules trapped within the network—a three-dimensional network swollen by a solvent. If the solvent is water, the gel is termed a "hydrogel".

Gels may be classified as either a chemical gel or a physical gel. The former are formed by chemical covalent bonds, resulting in a product called covalently cross-linked gels, and are not reversible. The latter are formed by secondary physical forces, such as hydrogen bonding or hydrophobic or charge interactions, and are reversible. Commercially available block copolymers of poly(ethylene oxide-b-propylene oxide-b-ethylene oxide) (PEO/PPO/PEO; Pluronics (BASF, Mount Olive, N.J.) or Poloxamers (ICI) are the best known examples of reversible, thermally gelling polymers. PEO/PPO/PEO copolymers are a family of more than 30 different nonionic surfactants, covering a wide range of liquids, solids and pastes with molecular weights ranging from about 1000 to 14,000. Concentrated solutions of PEO/PPO/PEO copolymers form reversible gels at high temperatures and revert to liquid state upon lowering of temperature. Gelation temperature depends on polymer composition and solution concentration.

Aqueous solutions of PEO/PPO/PEO copolymers demonstrate phase transitions from sol to gel (low temperature sol-gel boundary) and gel to sol (high temperature gel-sol boundary) with monotonically increasing temperature when the polymer concentration is above a minimum critical value. The mechanism of gelation of PEO/PPO/PEO copolymers is still uncertain.

Thermoreversible gels are also formed by several naturally occurring polymers such as gelatin (a protein prepared from partial hydrolysis of collagen), polysaccharides such as agarose, amylopectin, carrageenans, Gellan™, and the like. All of this class of biopolymers form hydrogels when cooled. By contrast, cellulose derivatives gel by a different mechanism: they are sols at low temperatures and become gels at high temperatures. The sol-gel transition temperature is affected by substitutions at the hydroxyl group of cellulose.

Novel biodegradable triblock copolymers of polyethylene glycol and poly(lactic/glycolic acid)(PEG/PLGA/PEG) were developed, and as aqueous solutions exhibit sol to gel transition at body temperature. A nonresorbable thermoreversible gel based on copolymers of N-isopropylacrylamide with acrylic acid (poly(NiPAAm-co-AAc)) have been developed, and demonstrate reversible sol-to-gel transition at physiological temperature ranges due to lower critical solution temperatures exhibited by polymers of the N-isopropylacrylamide.

As an example of a different gelling mechanism, charged, water soluble polymers may form reversible gels in response to pH change in solution. For example, chitosan solutions exhibit a sol-to-gel transition at a pH of about 7.0, when pH changes from slightly acidic to neutral. The pH-triggered transition is slower than the transition caused by changes in temperature.

Chemically cross-linked gels are used extensively as matrices in chromatography and electrophoreses analytical methods to separate molecules according to molecular weight and charge. Additionally, efforts have been made to deliver drugs to human patients via reversibly gelling polymers, as well as topical applications and for ophthalmic delivery of therapeutic agents. It is known to use copolymer polyols which are available commercially under the trade name Pluronic™, as described in U.S. Pat. No. 4,188,373.

In-situ gelling compounds have been proposed for use in implantation of drug delivery systems (for example, in cancer treatment), as well as injectable matrices for tissue engineering. Stimulus induced in-vivo gelation is a process that produces no toxic polymerization residues and results in no heat generation.

For example, U.S. Pat. No. 5,252,318 discloses a reversibly gelling aqueous composition that undergoes significant viscosity changes to simultaneous changes in both temperature and pH. The '318 composition is comprised of a combination of at least two separate and distinct reversibly gelling polymers-one of which is temperature sensitive (such as methyl cellulose or block copolymers of polyoxyethylene and polyoxypropylene) and the other being pH sensitive (such as a polyacrylic acid). The composition is intended for use as drop instillable, oral and injectable drug delivery vehicles, and for topically applied lubricants, wetting agents and cleaning agents.

Other approaches to injectable polymers have included single-stimulus polymers, as for example in U.S. Pat. No. 5,939,485. Gelation of the aqueous polymer solution is responsive to a change in a single environmental stimulus, such as temperature, pH or ionic strength.

U.S. Pat. No. 4,732,930 discloses a chemically cross-linked gel composition comprised of a polymerized product that is obtained by polymerization of isopropylacrylamide monomer, a source of metal ions, a crosslinking agent and a liquid medium. The product exhibits a reversible phase transition function that results in a drastic volume change in response to changes of the liquid medium composition temperature or ion concentration.

U.S. Pat. No. 5,525,334 discloses a method for vascular embolization by introduction of an aqueous solution of a thermosensitive polymer which gels in vivo at the body temperature of a patient. Obviously, such a thermosensitive gelling response will be inoperative in a process wherein the polymer must travel a substantial distance within the patient's body prior to gelation (such as when the gel is introduced through a catheter running from the femoral artery to the brain).

PCT published application number WO 99/56783 discloses a hydrogel for the treatment of aneurysms, whereby the gel carries both a radiopaque agent (permitting the radiogel to be visualized under fluoroscopy) and a therapeutic agent. The hydrogel is delivered through a catheter into an aneurysm, where the hydrogel becomes more viscous upon reaching body temperature or upon exposure to bodily fluids. The gelled compound blocks flow into the aneurysm, and can be adapted to deliver a human growth factor to promote growth of a cellular layer across the neck of the aneurysm.

It is therefore an object of the present invention to provide a single injectable aqueous gelling solution that is sensitive to at least two environmental stimuli, and more preferably, a compound that is sensitive to at least two in vivo environmental stimuli in a human or other mammalian body. The compound of the present invention will gel when exposed to critical minimum values of the environmental stimuli and is preferably a reversibly gelling compound, such that when the critical minimum values of all (or at a minimum, at least one) of the environmental stimuli fall below or outside the range of sensitivity, the gelled compound returns to an un-gelled condition.

The ideal multiple stimulus reversible hydrogel comprises an aqueous-based solution or compound having low viscosity at formation conditions, but exhibits rapid gelation at physiological conditions. It gels in response to multiple in-situ environmental stimuli, and is reversible. It must have reasonable mechanical strength and have biocompatibility with the host tissue.

The following references disclose processes or compounds useful in this art:

U.S. Pat. No. 5,525,334

U.S. Pat. No. 5,702,361

U.S. Pat. No. 5,695,480

U.S. Pat. No. 5,858,746

U.S. Pat. No. 5,589,568

T. G. Park and A. S. Hoffman, "Synthesis, Characterization, and Application of pH/Temperature-sensitive Hydrogels", Proceed. Intern. Symp. Control. Rel. Bioact. Mater., 17 (1990), pp 112–113.

G. Chen and A. S. Hoffman, "Graft Copolymers That Exhibit Termperature-induced Phase Transitions Over a Wide Range of pH", Vol 3, Nature, 1995, pp. 49–52.

S. Beltran, J. P. Baker, H. H. Hooper, H. W. Blanch and J. M. Prausnitz, "Swelling Equilibria for Weakly Ionizable, Temperature-Sensitive Hydrogels",Proc. Amer. Chem. Soc., 1991.

J. Zhang and N. A. Peppas, "Synthesis and Characterization of pH- and Temperature-Sensitive Poly(Methacrylic acid)/Poly(N-isopropylacrylamide) Interpenetrating Polymeric Networks, Macromolecules, 2000 (currently available on-line on the world wide web).

T. G. Park, "Temperature Modulated Protein Release From pH/Temperature Sensitive Hydrogels; Biomaterials 20 (1999), pp. 517–521.

SUMMARY OF THE INVENTION

The present invention comprises an aqueous polymeric solution capable of gelling upon exposure to a critical minimum value of a plurality of environmental stimuli. A "plurality" of environmental stimuli may be any number equal to or greater than two, although in most cases the process of the present invention will utilize two stimuli. The aqueous polymeric solution is capable of having gelation reversed if all, or at a minimum, at least one, of the environmental stimuli fall below (or outside a range of) critical minimum values. The environmental stimuli may be any stimulus that induces gelation, and is exemplified by temperature, pH, ionic strength, electrical field, magnetic field, solvent composition, chemical composition, light, pressure and the like. The critical minimum values for each of these stimuli may vary depending upon the local environment in which the gel is used, and will likely be markedly different between medical (or, in vivo) and industrial uses.

In vivo environmental stimuli may be either associated with human patients, or in veterinarian use with domestic or farm animals. For example, the product and process of the present invention may be used with cattle, horses, sheep, pigs, dogs, cats, and the like. The environmental stimuli may be either conditions that are naturally found within the area of use (e.g. "ambient"), or they may be externally imposed. Generally speaking, when injected into a human, the aqueous polymeric solution of the present invention is injected into a specific locus within the body—either a cavity (such as a post-operative tumor site) or a conduit/duct (such as a blood vessel) or into a tissue mass (such as a tumor).

The polymeric solution may either be a carrier for a pharmaceutically active therapeutic agent (in which case it will typically be an aqueous solution), or it may merely act as an inert blocking mass. An example of the former is the injection of chemicals or radioisotopes delivered through a catheter to a tumor mass; an example of the latter is injection of a gelled mass into a tubular body so as to cause a restriction therein (e.g. an aneurism of a blood vessel or the vas deferens for purposes of reversible sterilization in males). Likewise, the polymeric solution may be used in industrial situations wherein it may not be an aqueous solution.

It would be of great medical benefit in in vivo environments, if an aqueous polymeric solution could be transported in a catheter within the body for extended distances without gelation. For example, if it is desired to implant a quantity of radioisotope in a gelled mass within the brain, a catheter may be inserted into the patients femoral artery and the therapeutic agent is transported from that locale to the brain. Through use of the process of the present invention, for example, the two stimuli to induce gelation may be temperature and pH in the blood stream, such that warming of the liquid polymeric compound alone (within the catheter) will not cause gelation. It is not until the compound contacts the blood in the brain, and is induced by the pH or ionic strength of the blood to gel, that gelation occurs.

DETAILED DESCRIPTION OF THE INVENTION

Figure 1:
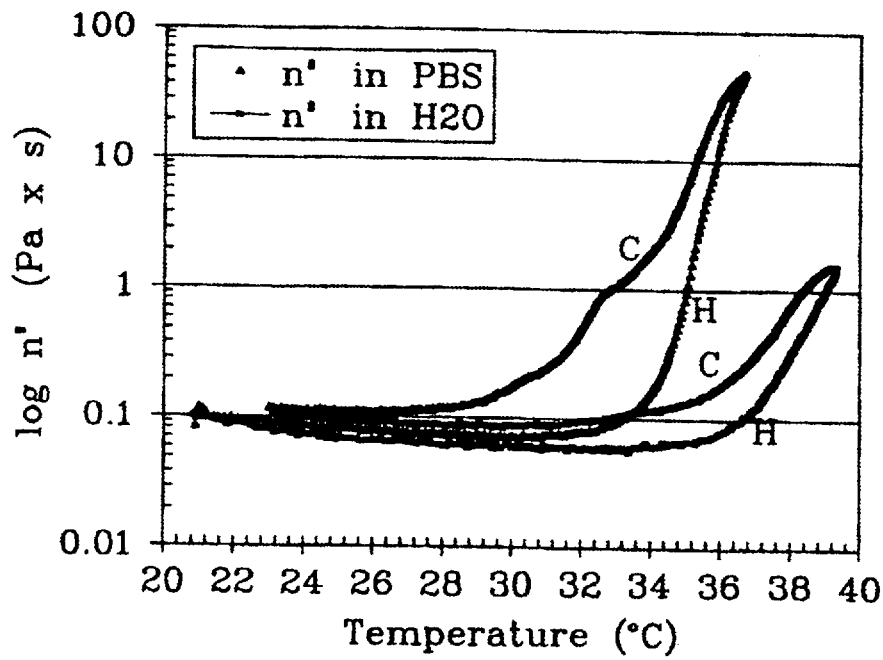
FIG. 1 is a graphical representation of the logarithm of storage viscosity (log n') versus temperature for poly (NIPAAm-co-DMAEA) polymer.

The reversible, stimulus-sensitive gels of the present invention are intended primarily for use in medical environments, such as the embolization of blood vessels at remote anatomical locations. However, it is to be understood that the gels of the present invention are not limited to medical applications—they will find uses outside medicine. For example, uses as drilling muds in the drilling of oil or other deep wells; subterranean use to block transport of noxious pollutants in an aquifer; the sealing of any industrial conduit to block passage of materials therein, and the like.

There are specific uses of gelling polymers wherein it is greatly preferred that the gelation response occur only when the polymer solution is exposed to multiple stimuli. As used herein, the stimuli may be any environmental stimulus that, in combination with at least one additional stimulus, causes the gelation reaction of a polymer solution. For example, such stimuli as temperature, pH, ionic strength, electrical field, magnetic field, solvent concentration/composition, surrounding chemical concentration/composition, light or pressure. While it is probably preferred in most cases that gelation result from two stimuli, it is within the context of the present invention that gelation occur in response to three or more stimuli.

As used herein, the stimuli responsible for gelation must reach a "critical minimum value" to effectively cause gelation. Values outside of this critical minimum value will cause the polymer composition to flow as (or similar to) a liquid. The critical minimum value will depend upon the particular environment—and the value for a single stimuli (for example, temperature) may be radically different depending upon the use. For example, in the context of a polymer solution injected into the blood stream of a human body wherein temperature and pH are the stimuli responsible for gelation, the critical minimum value for temperature is approximately 35–37° C. (internal body temperature) and the critical minimum value for pH is approximately 7.0–7.5 (the pH of blood and many other interstitial fluids). On the other hand, the critical minimum value for gelation in oil-field applications may be in excess of 70° C. and pH of less than 6.0 or greater than 8.0. For ease of description, and as described herein, any stimuli condition that falls outside that required for gelation is denoted as "below" or "less than" the critical minimum value, even though the value may be higher. For example, while room temperature may be on the order of 20° C. and therefore below the critical minimum value (37° C.) to induce gelation, a temperature of 50° C. may likewise inhibit gelation because it is too high, and as defined herein is also "below" the critical minimum value.

Gelation is the change in viscosity from a fluid-like composition to a solid-like composition. While the degree of "solidness" may vary from application to application, generally speaking gels of the present invention will exhibit viscosities in the full range of from paste-like to solid-like.

In certain situations, it is critical that gelation of the gel be reversible. For example, the pre-operative embolization of vessels for tumor treatment may be necessary to successfully shrink such tumors; it is not desired that blood flow be forever blocked in such vessels due to severe tissue damage. Upon return to environmental stimuli conditions that are "below" the critical minimum values, the gel reverses its viscosity and returns to a solution that is transportable within its immediate environment. The gels of the present invention are highly stable and do not exhibit phase separation upon standing or upon repeated cycling between the liquid and gel state. It is especially important that once gelled in situ, that the gel composition remain gelled indefinitely, or until intentionally reversed. For example, it is anticipated that gels of the present invention can be designed that will remain gelled for as long as many years.

Also, as used herein, the word "environmental" refers to the myriad of stimuli that might induce gelation. In industrial, non-medical settings such environmental stimuli may comprise chemical composition, temperature, light, pressure, and the like. In the context of human or other mammalian bodies, the word "environmental" typically refers to well-known conditions within the body that can impact the gel (temperature, pH, ionic strength, etc.).

The polymers useful in the present invention include but are not limited to thermally reversible copolymers that are useful as a gel that forms without substantial syneresis when the thermally reversible copolymer is in an aqueous solution. Syneresis is defined as water expelled from a copolymer matrix upon gelation. Substantial syneresis is more than about 10 wt % water expelled from the copolymer matrix. According to the present invention, it is preferred that the syneresis be less than about 10 wt %, more preferably less than about 5 wt % and most preferably less than about 2 wt %. Substantially no syneresis is syneresis of less than about 2 wt %, preferably 0 wt %.

As an example of the sort of polymers that can be synthesized according to the present invention, and not intending to be limited by the recitation of specific compounds, the thermally reversible copolymer can be a linear random, block or graft copolymers of an [meth-]acrylamide derivative and a hydrophilic comonomer wherein the copolymer is in the form of a plurality of chains having a plurality of molecular weights greater than or equal to a minimum geling molecular weight cutoff. According to the present invention, the minimum geling molecular weight cutoff is at least several thousand and is preferably about 12,000. The presence of a substantial amount of copolymer or polymer chains having molecular weights less than the minimum geling molecular weight cutoff results in a milky solution that does not gel. Further, the amount of hydrophilic comonomer in the linear random copolymer is preferably less than about 10 mole %, more preferably less than about 5 mole % and most preferably about 2 mole %. When the hydrophyllic comonomer is AAc and the thermosensitive co-monomer is NiPAAm, the amount of AAc in the linear random copolymer is preferably from about 1 mole % to about 2.5 mole %, most preferably from about 1.6 mole % to about 1.9 mole %. The structure of linear chains is not cross linked. Moreover, the block or graft copolymer structure is one in which a linear chain is shared by randomly alternating portions of the [meth-]acrylamide derivative and the hydrophilic comonomer.

The [meth-]acrylamide derivative is an N-alkyl substituted [meth-]acrylamide including but not limited to N-isopropyl[meth-]acrylamide, N,N-diethyl [meth-]acrylamide, N-[meth-]acryloylpyrrolidine, N-ethyl[meth-]acrylamide, and combinations thereof.

The hydrophilic comonomer is any hydrophilic comonomer that co-polymerizes with the [meth-]acrylamide derivative. Preferred hydrophilic comonomers are hydrophilic [meth-]acryl-compounds including but not limited to carboxylic acids, [meth-]acrylamide, hydrophilic [meth-]acrylamide derivatives, hydrophilic [meth-]acrylic acid esters. The carboxylic acid may be, for example, acrylic acid, dimer of acrylic acid, methacrylic acid and combinations thereof. The hydrophilic acrylamide derivatives include but are not limited to N,N-diethyl[meth-]acrylamide, 2-[N,N-dimethylamino]ethyl [meth-]acrylamide, 2-[N,N-diethylamino]ethyl [meth-]acrylamide, or combinations thereof. The hydrophilic [meth-]acrylic esters include but are not limited to 2-[N,N-diethylamino]ethyl[meth-]acrylate, 2-[N,N-dimethylamino]ethyl [meth-]acrylate, and combinations thereof.

The polymer composition most likely having primary application in medical applications is a hydrogel, wherein water is the solvent. Obviously, introducing non-aqueous solvents into a human or other mammalian body can have significant side effects. However, in industrial settings, the solvent may comprise any well-known organic solvent.

In medical applications, the gels of the present invention may be utilized to deliver therapeutic agents to various body locations, including but not limited to intravenous and subcutaneous therapies, tissue supplementation, parenteral delivery, vascular and therapeutic embolization, tumor therapy, blockage of bodily conduits, and the like. Any biologically active compound having therapeutic qualities may be delivered by the process of the present invention, including but not limited to proteins, polypeptides, polynucleotides, polysaccharides, glycoproteins, lipoproteins, and the like.

Classes of therapeutically active or diagnostic compounds that will most likely be administered by the process of the present invention include but are not limited to anti-cancer drugs, radionuclides, antibiotics, immunosuppressants, neurotoxins, anti-inflammatory agents, imaging agents, and the like.

It is to be understood that while the biological uses of the products and processes of the present invention will find particular application with humans, other types of animals may be similarly treated. Because the cost of these procedures is relatively expensive, they typically will not be useful in a commercial sense with a broad range of animals. However, research applications of this technology with non-mammalians may be feasible. Other than humans, the invention will find particular application with cattle, horses, sheep, pigs, dogs, cats, and the like.

Generally speaking, compositions of polymers of the present invention will be found in very broad ranges. A reversible geling solution may be made by mixing the reversible polymer with an aqueous solution in an amount of about 70 wt % to 99 wt %.

EXAMPLE 1

N-isopropylacrylamide was recrystallized from n-hexane and dried under vacuum. Acrylic acid was distilled under reduced pressure. 2.2'-azobisisobutyronitrile was purified by recrystallization from methanol. Dioxane was sonicated, degased and purged with deoxygenated nitrogen prior to use. Either and hexane (reagent grade) were used as received. Phosphate-buffered saline (PBS) (pH=7.4) was made by dissolving 0.272 g of anhydrous $KH_2PO_4$, 2.130 g of $Na_2HPO_4 \cdot xH_2O$ and 8.474 g of NaCl in 1.0 liter of ultrapure water. pH of the solution was adjusted to 7.4 with ORION 720A pH-meter.

The copolymers were obtained by free-radical solution copolymerization of N-isopropylacrylamide (NIPAAlm) with a proper comonomer; 2-(dimethylamino) ethyl acrylate (DMAEA) for KK-11 copolymer and acrylic acid (Aac) for Mj-114 copolymer. A positively ionizable, weakly basic copolymer was synthesized in dioxane, using 97/3 mol % ratio of NIPAAm and DMAEA, using AIBN as a free-radical initiatio. The monomers (5.000 g, $4.415 \times 10^{-2}$ moles of NIPAAM and 207.3 uL, $1.365 \times 10^{-3}$ moles of DMAEA) were dissolved in dry, degassed dioxane (24 mL) and flushed with dry, deoxygenated nitrogen for 0.5 hour. After adding AIBN (4.8 mg, $2.93 \times 10^{-5}$ moles in dioxane solution (about 100 uL), the mixture was purged with nitrogen for additional 10 minutes. The polymerization was conducted at 70° C. for 19 hr under pure nitrogen. The reaction mixture was then cooled to RT, diluted with dioxane (24 mL), poured into 3/1 v/v mixture of ethyl ether/hexane and vigorously stirred for about 2 hours. The crude polymer was then filtered, washed with ether and dried in vacum overnight. Dry polymer was dissolved in 200 mL of UP water and filtered through a nylon membrane (pore size 0.45 um). Crude polymer solution was purified by ultrafiltration (three times) using a 30KD MWCO membrane. The purified solution was freeze-dried to obtain a dry polymer poweder (yield 84–85%).

The molar masses were analyzed by Gel Permeation Chromatography (GPC), using the following equipment:

two styragel columns, HMW 6E and HR 4E (7.8×300 mm both);

Rheodyne 50 or 200 ul loop injector;

Detectors: miniDAWN light scattering detector and Waters 410

Differential Refractometer;

515 HPLC Waters pump and isocratic THF (HPLC grade) mobile phase, sonicated and degassed; flow rate was set at 0.5 ml/min;

Astra 4.70 software.

The results are summarized in Table 1 below.

TABLE 1

| Molar mass analysis by gel permeation chromatography | | | |
|---|---|---|---|
| Sample ID | Polymer ID | Average Molar mass ($M_w$), g/mol | Poydispersity ($M_w/M_n$) |
| MJ-114 | poly(NIPA-co-AAc) | 1.14 ± 0.03 e + 05 | 1.024 ± 0.04 |
| KK-11 | poly(NIPA-co-DMAEA) | 6.37 ± 0.48 e + 05 | 1.05 ± 0.08 |

Reversible sol-gel transitions of the poly(NIPAAm-co-DMAEA) and poly(NIPAAm-co-Aac) polymer solutions were studied using dynamic rheology (Rheometric Scientific SR 2000). The polymer solutions were placed between parallel plates with diameter 2.5 mm and gap 0.5 mm. The Dynamic Temperature Ramp Test (DTRT) was conducted under controlled stress (2.0 dync/cm ) and frequency (1.0 radian/sec.). The heating-cooling cycle temperature gap was established for 21–37° C. with increment 0.3° C. A 10% polymer solution in water and PBS was investigated.

Figure 2:
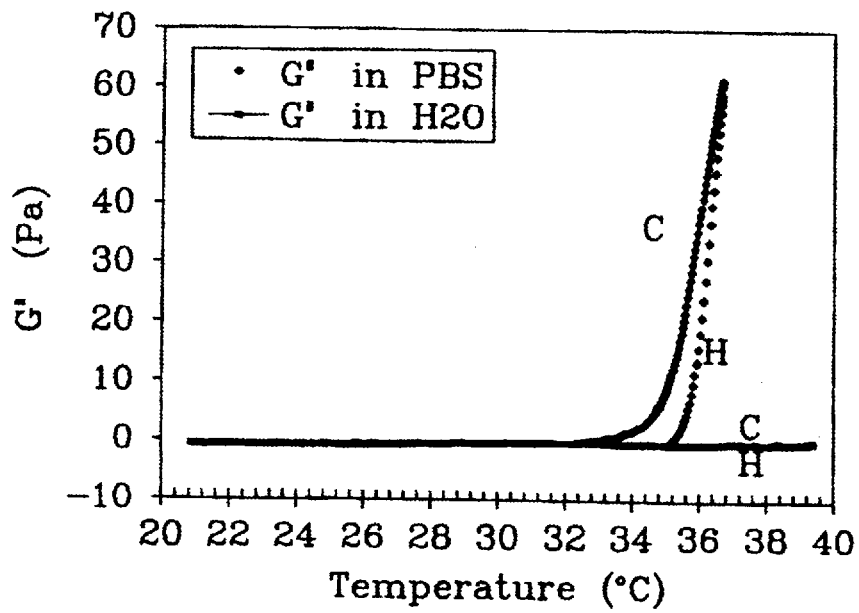
FIG. 2 is a graphical representation of the storage modulus (G') versus temperature for poly(NIPAAm-co-DMAEA) polymer.
Figure 3:
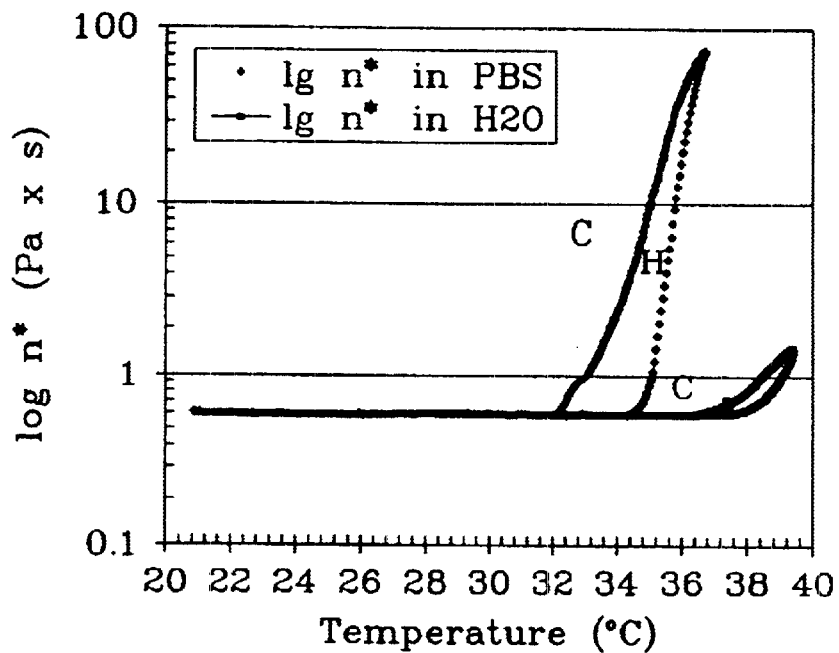
FIG. 3 is a graphical representation of the complex viscosity logarithm (log n*) versus temperature for poly (NIPAAm-co-DMAEA) polymer.

FIGS. 1–6 illustrate the results of DTRT conducted for poly(NIPAAm-co-DMAEA) and poly(NIPAAm-co-AAc) polymer solutions at temperature gap 21–37° C. FIG. 1 illustrates changes in the log of the storage viscosity (n') of poly(NIPAAm-co-DMAEA) (KK-11) polymer solution as a function of temperature. Heating process (H) causes sol to gel transition and, as a result, viscosity increases by three orders of magnitude (0.1–100 Paxs). The increase is very sharp and takes place at about 34–36.5° C. Upon cooling (C), the gel melts at a temperature that is lower than the gelation temperature indicating characteristic hysteresis loop between gel formation and gel melting temperatures. This behavior results from resistance to disintegration of entangled hydrogel molecules. This experiment was conducted under controlled stress (2.0 dyne/cm$^2$) and frequency (1.0 radian/sec). The heating-cooling cycle temperature increment was 0.3° C. FIG. 2 illustrates how the storage modulus changes as a function of temperature, under controlled stress (2.0 dyne/cm$^2$) and frequency (1.0 radian/sec). The heating-cooling cycle temperature increment was 0.3° C. FIG. 3 illustrates the logarithm of complex viscosity changes as a function of temperature, conducted under controlled stress (2.0 dyne/cm$^2$) and frequency (1.0 radian/sec). The heating-cooling cycle temperature increment was 0.3° C.

Figure 4:
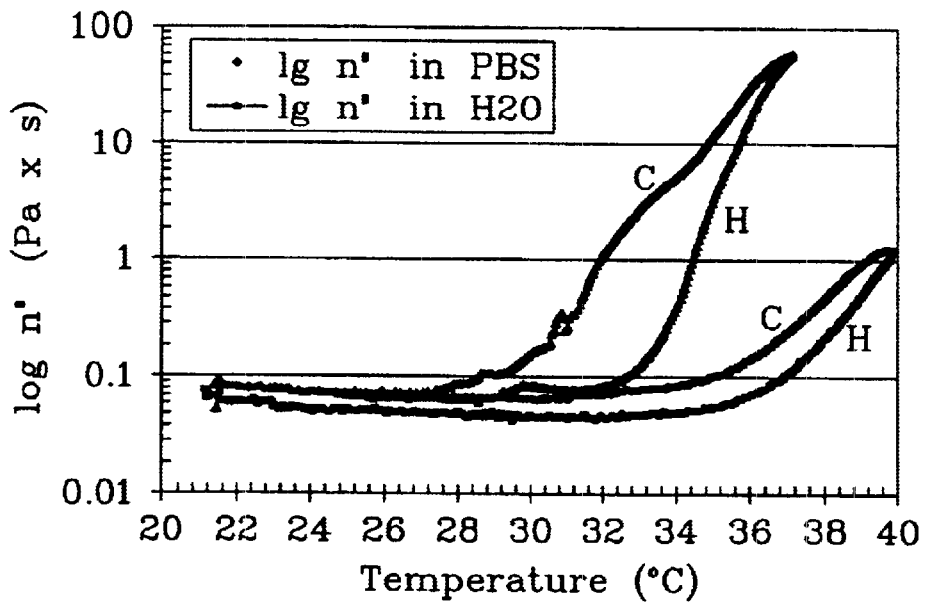
FIG. 4 is a graphical representation of the storage viscosity logarithm (log n') versus temperature for poly(NIPAAm-co-AAc) polymer.
Figure 5:
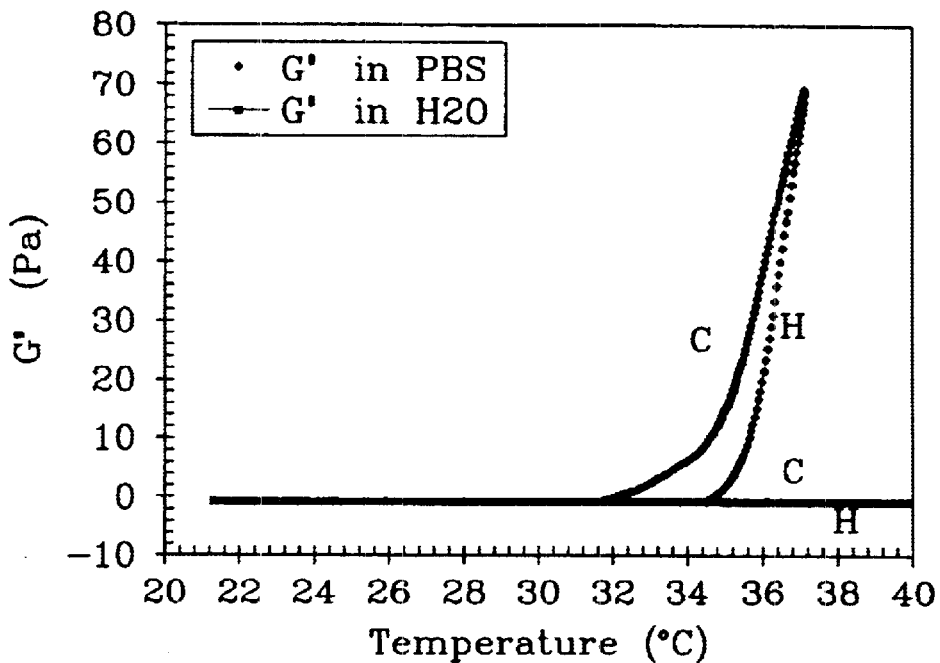
FIG. 5 is a graphical representation of the storage modulus (G') versus temperature for poly(NIPAAm-co-Aac) polymer.
Figure 6:
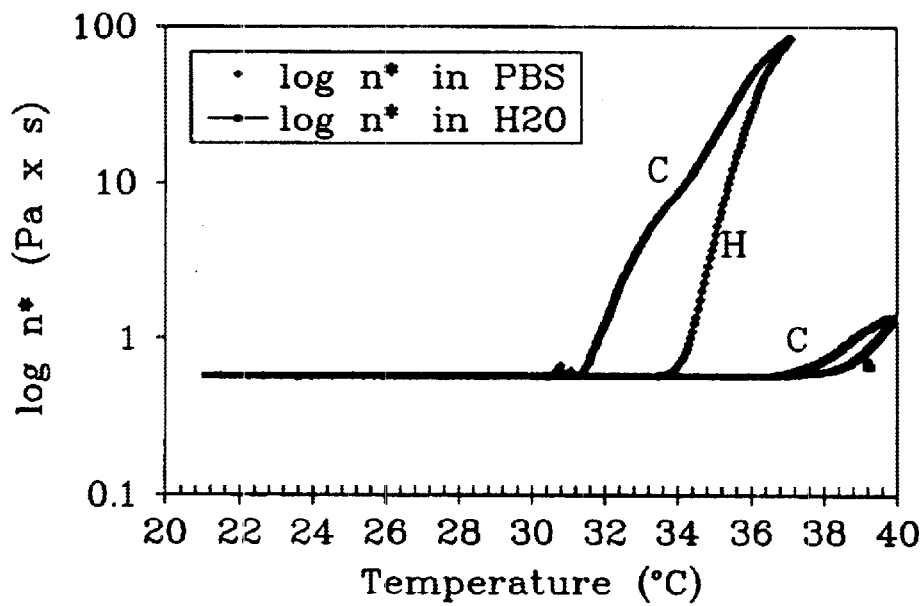
FIG. 6 is a graphical representation of the complex viscosity logarithm (log n*) versus temperature for poly (NIPAAm-co-Aac) polymer.

FIGS. 4–6 illustrate rheological behavior of poly (NIPAAm-co-Aac) (MJ 114 k) polymer solution. Each of the experiments of FIGS. 4–6 were conducted under controlled stress (2.0 dyne/cm$^2$) and frequency (1.0 radian/sec.). The heating-cooling cycle temperature increment was 0.3° C.

The properties illustrated in FIGS. 1–6 illustrate the benefits of the instant invention. A sharp sol to gel transition takes place just before the physiological temperature of the human body, and hysteresis helps to avoid quick melting of the formed gel due to small fluctuations of body temperature. The storage modulus (G') of two gels is practically zero at a sol state, so it is not shown on a heating curve. It appears and sharply increases at 32.0 and 32.5° C. for poly (NIPAAm-co-Aac) and poly(NIPAAm-co-DMAEA) gels solutions in PBS, as shown in FIGS. 2 and 5 respectively. For both gels, the maximum value of the storage modulus is at about 37° C., indicating that the material is susceptible for injectable gelling formulations.

Different behavior of the polymer solutions in water versus those in PBS proves that it is possible to deliver the water solution to a remote anatomical location via a long needle or catheter in a sol (non-gelled) state. The polymer water solution will gel upon contact with body fluids at physiological temperature.

EXAMPLE 2

A copolymer of N-isopropylacrylamide with hydrophilic comonomer, 2-(dimethylamino)ethyl acrylate (DMAEA) was synthesized in dioxane by a free radical polymerization. After a two-step extensive purification, by precipitation and ultrafiltration the NDAEA copolymer was lyophilized to obtain the copolymer in a powder form. This powder was then dissolved in water to form an aqueous solution.

A 2 ml sample of this solution, warmed up to 3.7° C., was placed in a 2 ml syringe equipped with a 30 Gauge needle. The needle was immersed in a phosphate buffered saline (PBL) solution also warmed up to 37° C. The warm copolymer solution from the syringe was injected into the warm PBS solution. Instantaneous gel formation was observed; the injected gel formed a "string".

An additional 2 ml sample of the same aqueous solution was heated gradually from room temperature up to 40° C. No gel formation was observed even at 40° C.

Yet another 2 ml sample of the same solution, equilibrated at room temperature, was placed in a 2 ml syringe equipped with a 30 Gauge needle. The needle was immersed in a phosphate buffered saline (PBs) solution also equilibrated at room temperature. The room temperature copolymer solution from the syringe was injected into the room temperature PBS solution. No gel formation was observed-the injected polymer solution simply dissolved in the buffer.

Thus, the impact of multiple stimulus gelation is evident in temperature and proper ionic strength is required to cause gelation of the NDAEA copolymer. Change in only one stimuli was ineffective to cause gelation.

EXAMPLE 3

A copolymer of N-isopropylacrylamide with hydrophilic comonomer, 2-(N,N-dimethylamino)ethyl acrylate (NDAEA) was synthesized in dioxane by a free-radical polymerization. After a two-step extensive purification, by precipitation and ultrafiltration, the NDAEA copolymer was lyophilized to obtain the copolymer in powder form. This powder was then dissolved in water to form an aqueous solution.

A 2 ml sample of this solution, warmed to 37° C., was placed in a 2 ml syringe equipped with a 30 Gauge needle. The needle was immersed in a PBS solution also warmed up to 37° C. The warm copolymer solution from the syringe was injected into the warm PBS solution. Instantaneous gel formation was observed, the injected gel forming a "string". Another 2 ml sample of the same aqueous solution was heated gradually from room temperature up to 40° C. No gel formation was observed even at 40° C.

Yet another 2 ml sample of the solution, equilibrated at room temperature, was placed in a 2 ml syringe equipped with a 30 Gauge needle. The needle was immersed in a PBS solution also equilibrated at room temperature. The room temperature copolymer solution from the syringe was injected into the room temperature PBS solution. No gel formation was observed; the injected polymer solution simply dissolved in the buffer.

CLOSURE

Having thus described a preferred exemplary embodiment of the present invention, it should be noted by those skilled in the art that the disclosures herein are exemplary only and that alternatives, adaptations and modifications may be made within the scope of the present invention. Thus, the present invention is not to be limited to the specific embodiments illustrated herein, but solely by the scope of the claims appended hereto.

We claim:

1. A polymeric compound that remains a solution until exposed to critical minimum values of at least two environmental stimuli, wherein a single polymer forms a gel upon exposure to the critical minimum values of the at least two environmental stimuli.

2. The polymeric compound of claim 1, wherein the at least two environmental stimuli are selected from the group consisting of temperature, pH, ionic strength, electrical field, magnetic filed, solvent composition, light, pressure and chemical composition of the ambient environment.

3. The polymeric compound of claim 1, wherein gelation reverses when one of the at least two environmental stimuli falls below the critical minimum value.

4. The polymeric compound of claim 1, wherein the polymeric compound forms a gel upon exposure to critical minimum values of at least two ambient environmental stimuli.

5. The polymeric compound of claim 1, wherein the polymeric compound forms a gel upon exposure to critical minimum values of at least two in vivo environmental stimuli.

6. The polymeric compound of claim 1, wherein the polymeric compound forms a gel upon exposure to critical minimum values of at least two in vivo environmental stimuli that are imposed externally.

7. The polymeric compound of claim 1, wherein the at least two environmental stimuli are in vivo conditions found in non-human mammalian bodies.

8. The polymeric compound of claim 1, wherein the at least two environmental stimuli are in vivo conditions found in human mammalian bodies.

9. The polymeric compound of claim 1, wherein the polymeric compound when in solution form, is injected into a specific locus in a human body.

10. A polymeric compound comprising:
   an aqueous polymeric solution upon exposure to a critical minimum value of a single environmental stimuli;
   a gel upon exposure of the polymeric solution to critical minimum values of at least two environmental stimuli; and
   wherein the gel forms the aqueous polymeric solution upon exposure of the gel to at least one of the at least two environmental stimuli falling below the critical minimum value.

11. The compound of claim 10, wherein the at least two environmental stimuli are selected from the group consisting of temperature, pH, ionic strength, electrical field, magnetic filed, solvent composition, light, pressure and chemical composition of the ambient environment.

12. The compound of claim 10, wherein the aqueous polymeric solution is injected into an aneurysm.

13. The compound of claim 10, wherein the aqueous polymeric solution forms the gel upon exposure to critical minimum values of at least two in vivo environmental stimuli.

14. The compound of claim 10, wherein the aqueous polymeric solution forms the gel upon exposure to critical minimum values of at least two in vivo environmental stimuli that are imposed externally.

15. The compound of claim 10, wherein the at least two environmental stimuli are in vivo conditions found in non-human mammalian bodies.

16. The compound of claim 10, wherein the at least two environmental stimuli are in vivo conditions found in non-human mammalian bodies.

17. The compound of claim 10, wherein the compound is injected into a specific locus in a human body when the compound comprises the aqueous polymeric solution.

18. A method of forming a gel from a polymeric compound in solution form, comprising:
   exposing the polymeric compound in solution form to critical minimum values of at least two environmental stimuli to form a gel, wherein the polymeric compound in solution form remains in solution form when exposed to a critical minimum value of less than at least two environmental stimuli.

19. The method of claim 18, further comprising selecting the environmental stimuli from the group consisting essentially of temperature, pH, ionic strength, electrical field, magnetic field, solvent compositions, chemical compositions, light, and pressure.

20. The method of claim 18, further comprising exposing the environmental stimuli in vivo within a mammalian body.

21. The method of claim 18, further comprising injecting the polymeric compound in solution form into a specific locus in a mammalian body and providing the environmental stimuli externally from the mammalian body.

22. The method of claim 18, further comprising injecting the polymeric compound in solution form into a specific locus in a human body.

23. The method of claim 18, further comprising injecting the polymeric compound in solution form to achieve therapeutic embolization.

24. The method of claim 18, further comprising placing a therapeutically active agent for treatment of a medical condition into a solution of the polymeric compound.

25. The method of claim 18, further comprising placing a radioisotope for treatment of a medical condition into a solution of the polymeric compound.

26. The method of claim 18, further comprising providing the polymeric compound as an aqueous solution.

27. The method of claim 18, further comprising providing a acrylamide derivative and a hydrophilic comonomer to form the polymeric compound.

28. The method of claim 18, further comprising providing the polymeric compound as a copolymer of 2-(N,N-dimethylamino)-ethylacrylate (DMAEA) and N-isopropylacrylamide.

29. A method of forming a reversible gel from a polymer in solution form, comprising:
   exposing the polymer in solution form to critical minimum values of at least two environmental stimuli to form a gel, wherein the polymer remains a solution when exposed to a critical minimum value of less than at least two environmental stimuli; and
   reducing the value of at least one of the at least two environmental stimuli below the critical minimum value thereby reversing gelation of the gel to the polymer in solution form.

30. The method of claim 1, further comprising providing a acrylamide derivative and a hydrophilic comonomer to form the polymeric compound.

31. The method of claim 1, further comprising providing the polymeric compound as a copolymer of 2-(N,N-dimethylamino)-ethylacrylate (DMAEA) and N-isopropylacrylamide.

* * * * *

UNITED STATES PATENT AND TRADEMARK OFFICE
CERTIFICATE OF CORRECTION

PATENT NO. : 6,660,247 B1
APPLICATION NO. : 09/603730
DATED : December 9, 2003
INVENTOR(S) : Anna Gutowska and Karol J. Krzyminski It is certified that error appears in the above-identified patent and that said Letters Patent is hereby corrected as shown below:

In the Specification:

Column 8, line 54, "(2.0 dync/cm )" should read --(2.0 dync/cm$^2$)--.

Column 9, line 50, "3.7° C" should read --37°C--.

In the Claims:

Column 12, line 27, claim 27, "acrylamide" should be --[meth]acrylamide--.

Column 12, line 45, claim 30, "acrylamide" should be --[meth]acrylamide--.

Signed and Sealed this

Twenty-fourth Day of October, 2006

JON W. DUDAS
*Director of the United States Patent and Trademark Office*